United States Patent [19]
Hubbell et al.

[11] Patent Number: 5,593,839
[45] Date of Patent: Jan. 14, 1997

[54] COMPUTER-AIDED ENGINEERING SYSTEM FOR DESIGN OF SEQUENCE ARRAYS AND LITHOGRAPHIC MASKS

[75] Inventors: Earl A. Hubbell, Mt. View; Robert J. Lipshutz, Palo Alto; Macdonald S. Morris, San Jose; James L. Winkler, Palo Alto, all of Calif.

[73] Assignee: Affymetrix, Inc., Santa Clara, Calif.

[21] Appl. No.: 460,411

[22] Filed: Jun. 2, 1995

Related U.S. Application Data

[62] Division of Ser. No. 249,188, May 24, 1994.

[51] Int. Cl.$^6$ ............... C12Q 1/68; C07H 21/04; G03F 9/00
[52] U.S. Cl. .............. 435/6; 430/5; 435/287.2; 536/24.3; 536/25.3; 935/88
[58] Field of Search ............ 435/6, 287.2; 536/24.3, 536/25.3; 935/88; 430/5

[56] References Cited

U.S. PATENT DOCUMENTS

| | | | |
|---|---|---|---|
| 5,143,854 | 9/1992 | Pirrung et al. | 436/518 |
| 5,235,626 | 8/1993 | Flamholz et al. | 378/34 |
| 5,288,514 | 2/1994 | Ellman | 427/2 |

FOREIGN PATENT DOCUMENTS

| | | | |
|---|---|---|---|
| WO92/10092 | 6/1992 | WIPO | A01N 1/02 |
| WO92/10588 | 6/1992 | WIPO | C12Q 1/68 |

OTHER PUBLICATIONS

USSN 08/143,312 filed Oct. 26, 1993, entitled "Arrays of Nucleic Acid Probes on Biological Chips."
Fodor et al. "Light–Directed, Spatially Addressable Parallel Chemical Synthesis," *Science* (1991) 251:767–773.
Brown et al., "An Inexpensive MSI/LSI Mask Making System," Symposium Proceedings University Government Industry Microelectronics Symposium, pp. III–31 to III–38 (1981).

*Primary Examiner*—George C. Elliott
*Assistant Examiner*—John S. Brusca
*Attorney, Agent, or Firm*—Townsend & Townsend & Crew LLP

[57] ABSTRACT

An improved set of computer tools for forming arrays. According to one aspect of the invention, a computer system is used to select probes and design the layout of an array of DNA or other polymers with certain beneficial characteristics. According to another aspect of the invention, a computer system uses chip design files to design and/or generate lithographic masks.

16 Claims, 14 Drawing Sheets

Microfiche Appendix Included
(5 Microfiche, 478 Pages)

COMPUTER-AIDED ENGINEERING SYSTEM FOR DESIGN OF SEQUENCE ARRAYS AND LITHOGRAPHIC MASKS

GOVERNMENT RIGHTS NOTICE

Portions of the material in this specification arose in the course of or under contract nos. 92ER81275 (SBIR) between Affymetrix, Inc. and the Department of Energy and/or H600813-1, -2 between Affymetrix, Inc. and the National Institutes of Health.

CROSS-REFERENCE TO RELATED APPLICATIONS

This application is a Rule 60 Division of application Ser. No. 08/249,188, filed May 24, 1994, and assigned to the assignee of the present invention.

COPYRIGHT NOTICE

A portion of the disclosure of this patent document contains material which is subject to copyright protection. The copyright owner has no objection to the xeroxographic reproduction by anyone of the patent document or the patent disclosure in exactly the form it appears in the Patent and Trademark Office patent file or records, but otherwise reserves all copyright rights whatsoever.

MICROFICHE APPENDIX

Microfiche Appendices A to AA comprising five (5) sheets, totalling 478 frames are included herewith.

BACKGROUND OF THE INVENTION

The present inventions relate to the field of computer systems. More specifically, in one embodiment the invention provides a computer-aided engineering system that generates the design of sequence arrays on a substrate, as well as the design of lithographic masks therefor.

Devices and computer systems for forming and using arrays of materials on a substrate are known. For example, PCT application WO92/10588, incorporated herein by reference for all purposes, describes techniques for sequencing nucleic acids and other materials. Such materials may be formed in arrays according to the methods of, for example, the pioneering techniques disclosed in U.S. Pat. No. 5,143,854, also incorporated herein by reference for all purposes. According to one aspect of the techniques described therein, an array of probes such as nucleic acids are fabricated at known locations on a chip. A labelled biological material such as another nucleic acid is contacted with the chip. Based upon the locations where the biological material binds to the chip, it becomes possible to extract information such as the monomer sequence of, for example, DNA or RNA. Such systems have been used to form, for example, arrays of DNA that may be used to study and detect mutations relevant to the detection of cystic fibrosis, detection of mutations in the P53 gene (relevant to certain cancers), HIV detection, and other genetic characteristics. Exemplary applications of such systems are provided in U.S. Ser. No. 08/143,312 (pending), and U.S. Pat. No. 5,288,514, incorporated herein by reference for all purposes.

Such techniques have met with substantial success, and in fact are considered pioneering in the industry. Certain challenges have been met, however, in the process of gathering, assimilating, and using the huge amounts of information now made available by these dramatically improved techniques. Existing computer systems in particular have been found to be wanting in their ability to design, form, assimilate, and process the vast amount of information now used and made available by these pioneering technologies.

Improved computer systems and methods for operating such computer systems are needed to design and form arrays of biological materials.

SUMMARY OF THE INVENTION

An improved computer-aided engineering system is disclosed. The computer system provides, among other things, improved sequence and mask generation techniques, especially computer tools for forming arrays of materials such as nucleic acids or peptides.

According to one aspect of the invention, the computer system is used to design and form the masks used in such studies. In another aspect of the invention, a computer system is used to select and design the layout of an array of nucleic acids or other biological polymers with certain beneficial characteristics.

According to one specific aspect of the invention a method of forming a lithographic mask is provided. The method includes the steps of, in a computer system, generating a mask design file by the steps of:

inputting sequence information to the computer system, the sequence information defining monomer addition steps in a polymer synthesis;

evaluating locations of the mask for opening locations used to perform said synthesis and joining the opening locations to adjust other opening locations;

outputting a mask design file, the mask design file defining locations for openings in the lithographic mask; and using the mask design file to form the lithographic mask, whereby at least some flash locations on the mask are connected.

Another embodiment of the invention provides a method of designing a synthesis process for an array of materials to be synthesized on a substrate, the array formed from groups of diverse biological materials. The method includes the steps of inputting a genetic sequence to a design computer system; determining a sequence of monomer additions in the computer by the steps of:

identifying a monomer addition template; and for monomer additions in the template, determining if the monomer additions are needed in formation of the genetic sequence and, if not, removing the monomer additions from the template;

generating an output file comprising a series of desired monomer additions; and providing the series of monomer additions as an input file (directly or indirectly) to a synthesizer.

Another embodiment of the invention provides a method of designing and using a synthesis sequence for a biological polymer. The method is conducted in a digital computer and includes the steps of identifying a series of monomer additions for adjacent synthesis regions on a substrate; adjusting the series of monomer additions to reduce the number of monomer additions that differ between at least two adjacent synthesis regions; and using the adjusted series of monomer additions to form the substrate.

A method of designing an array and its method of synthesis is also disclosed. The method includes the steps of inputting a genetic sequence file; identifying locations in the array for formation of genetic probes corresponding to the genetic sequence and selected mutations thereof; determining a sequence of monomer additions for formation of the probes and the selected mutations thereof; outputting at least one computer file representing the locations and the sequence of monomer additions; and using the at least one computer file to form the array.

A further understanding of the nature and advantages of the inventions herein may be realized by reference to the remaining portions of the specification and the attached drawings.

DESCRIPTION OF THE PREFERRED EMBODIMENTS

Contents

I. General

II. Target Selection

III. Layout

IV. Mask Design

V. Synthesis

VI. Scanning

I. General

Figure 1:
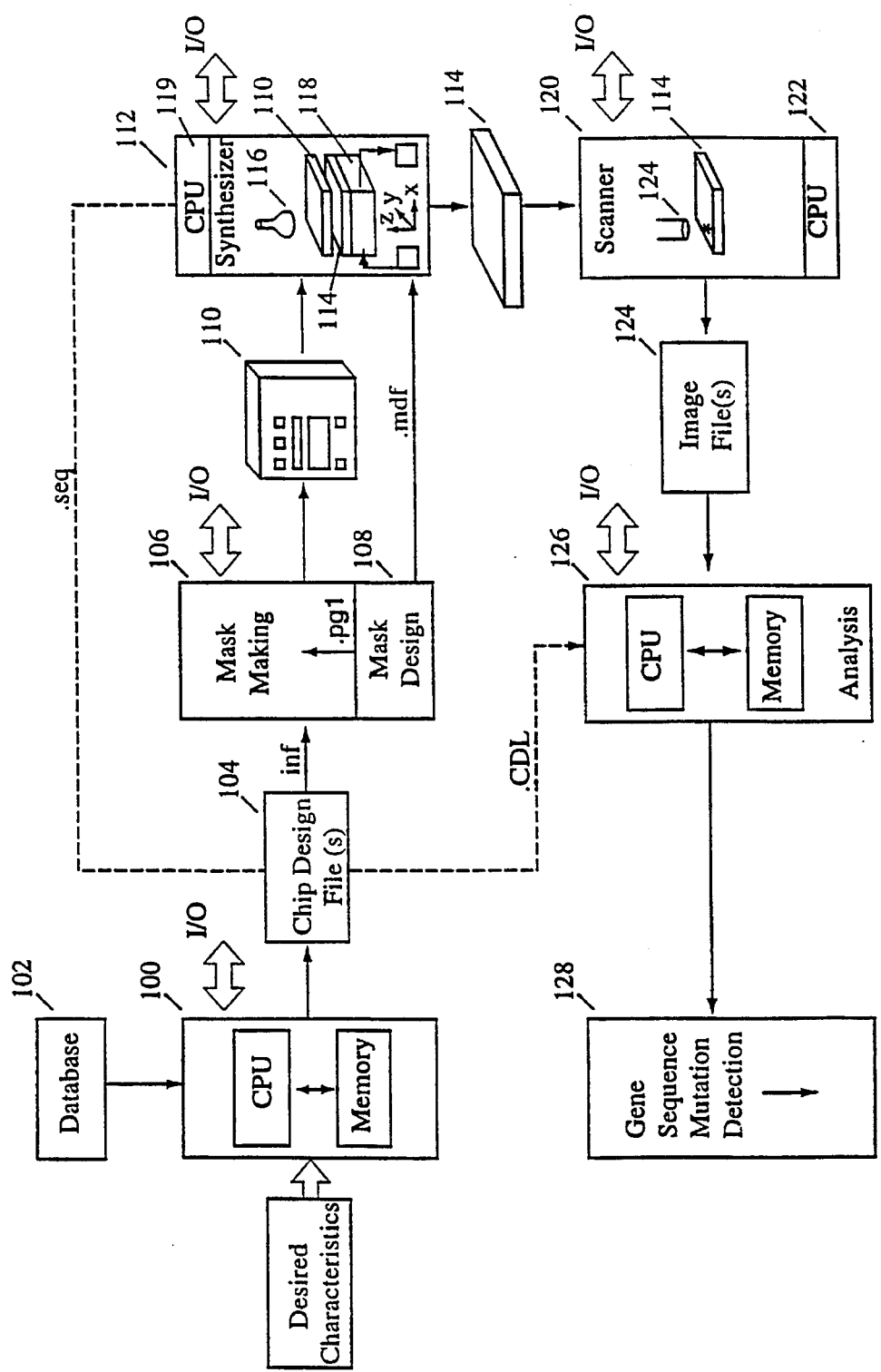
FIG. 1 illustrates the overall system and method of operation thereof.

FIG. 1 illustrates a computerized system for forming and analyzing arrays of biological materials such as RNA or DNA. A computer 100 is used to design arrays of biological polymers such as RNA or DNA. The computer 100 may be, for example, an appropriately programmed Sun Workstation or personal computer or work station, such as an IBM PC equivalent, including appropriate memory and a CPU. The computer system 100 obtains inputs from a user regarding desired characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 1, such equipment may or may not be located at the same physical site, but is shown together for ease of illustration in FIG. 1. The system 106 generates masks 110 such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed digital computer 119, which may or may not be the same computer as the computer(s) used in mask design and mask making.

The substrates fabricated by synthesis system 112 are optionally diced into smaller chips and exposed to marked receptors. The receptors may or may not be complementary to one or more of the molecules on the substrate. The receptors are marked with a label such as a fluorescein label (indicated by an asterisk in FIG. 1) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled receptor (*) has bound to the substrate. The output of scanner 120 is an image file(s) 124 indicating, in the case of fluorescein labelled receptor, the fluorescence intensity (photon counts or other related measurements, such as voltage) as a function of position on the substrate. Since higher photon counts will be observed where the labelled receptor has bound more strongly to the array of polymers, and since the monomer sequence of the polymers on the substrate is known as a function of position, it becomes possible to determine the sequence(s) of polymer(s) on the substrate that are complementary to the receptor.

The image file 124 is provided as input to an analysis system 126. Again, the analysis system may be any one of a wide variety of computer system(s), but in a preferred embodiment the analysis system is based on a Sun Workstation or equivalent. Using information regarding the molecular sequences obtained from the chip design files and the image files, the analysis system performs one or more of a variety of tasks. In one embodiment the analysis system compares the patterns of fluorescence generated by a receptor of interest to patterns that would be expected from a "wild" type receptor, providing appropriate output 128. If the pattern of fluorescence matches (within limits) that of the wild type receptor, it is assumed that the receptor of interest is the same as that of the wild type receptor. If the pattern of fluorescence is significantly different than that of the wild type receptor, it is assumed that the receptor is not wild type receptor. The system may further be used to identify specific mutations in a receptor such as DNA or RNA, and may in some embodiments sequence all or part of a particular receptor de novo.

Figure 2A:
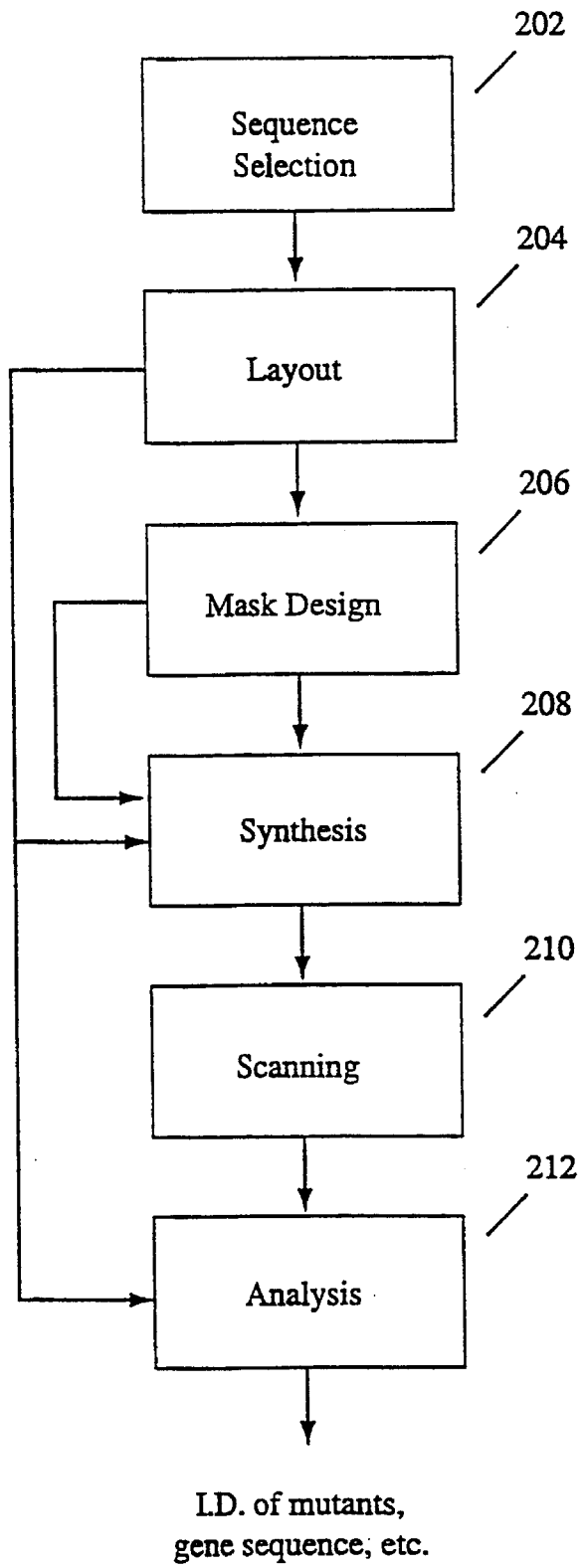
FIG. 2A is an illustration of the overall operation of the software involved in the system.

FIG. 2A provides a simplified illustration of the software system used in operation of one embodiment of the invention. As shown in FIG. 2A, the system first identifies the genetic sequence(s) that would be of interest in a particular analysis at step 202. The sequences of interest may, for example, be normal or mutant portions of a gene, genes that identify heredity, provide forensic information, or the like. Sequence selection may be provided via manual input of text files or may be from external sources such as GenBank. At step 204 the system evaluates the gene to determine or assist the user in determining which probes would be desirable on the chip, and provides an appropriate "layout" on the chip for the probes. The layout will implement desired characteristics such as minimization of edge effects, ease of synthesis, and/or arrangement on the chip that permits "reading" of genetic sequence.

At step 206 the masks for the synthesis are designed. Again, the masks will be designed to implement one or more desired attributes. For example, the masks may be designed to reduce the number of masks that will be needed, reduce the number of pixels that must be "opened" on the mask, and/or reduce the number of exposures required in synthesis of the mask, thereby reducing cost substantially.

At step 208 the software utilizes the mask design and layout information to make the DNA or other polymer chips. This software 208 will control, among other things, relative translation of a substrate and the mask, the flow of desired reagents through a flow cell, the synthesis temperature of the flow cell, and other parameters. At step 210, another piece of software is used in scanning a chip thus synthesized and exposed to a labeled receptor. The software controls the scanning of the chip, and stores the data thus obtained in a file that may later be utilized to extract sequence information.

At step 212 the software system utilizes the layout information and the fluorescence information to evaluate the chip. Among the important pieces of information obtained from DNA chips are the identification of mutant receptors, and determination of genetic sequence of a particular receptor.

Figure 2B:
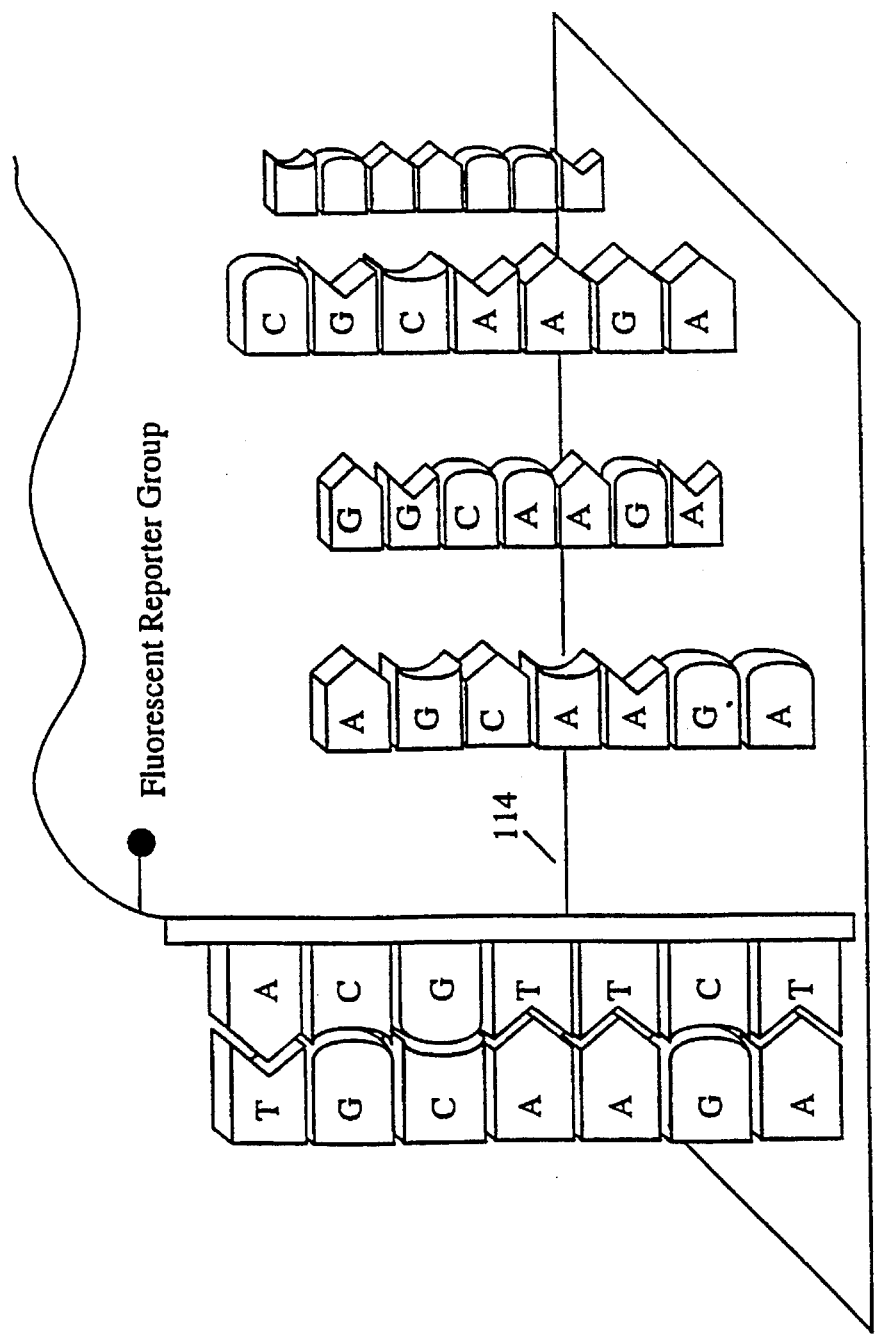
FIG. 2B illustrates conceptually the binding of probes on chips.

FIG. 2B illustrates the binding of a particular target DNA to an array of DNA probes 114. As shown in this simple example, the following probes are formed in the array:

```
                3'- AGAACGT
                    AGAACGA
                    AGAACGG
                    AGAACGC
                       .
                       .
                       .
```

When a fluorescein-labelled (or other marked) target with the sequence 5'-TCTTGCA is exposed to the array, it is complementary only to the probe 3'-AGAACGT, and fluorescein will be found on the surface of the substrate where 3'-AGAACGT is located. By contrast, if 5'-TCTTGCT is exposed to the array, it will bind only (or most strongly) to 3'-AGAACGA. By identifying the location where a target hybridizes to the array of probes most strongly, it becomes possible to extract sequence information from such arrays using the invention herein.

II. Target Selection

The target(s) of interest will be selected according to a wide variety of methods. For example, certain targets of interest are well known and included in public databases such as GenBank or a similar commercial database. Other targets of interest will be identified from journal articles, or from other investigations using VLSIPS™ chips, or with other techniques. According to one embodiment the target(s) of interest are provided to the system via an ASCii text file. The target may be evaluated in full, or only a portion thereof will be evaluated in some circumstances. Exemplary targets include those which identify a particular genetic tendency, characteristic, or disease, as well as a virus, organism, or bacteria type. Targets of particular interest include those wherein a large number of different, possible mutations are indicative of a particular tendency or disease.

In other cases, the target will not be specifically identified, but only known to be one of a number of possibilities. In such cases arrays may be synthesized to determine which of the number of possible targets is the "correct" target or if one of the targets is present.

III. Layout (MMDesign™, MMLayout™)

Figure 3:
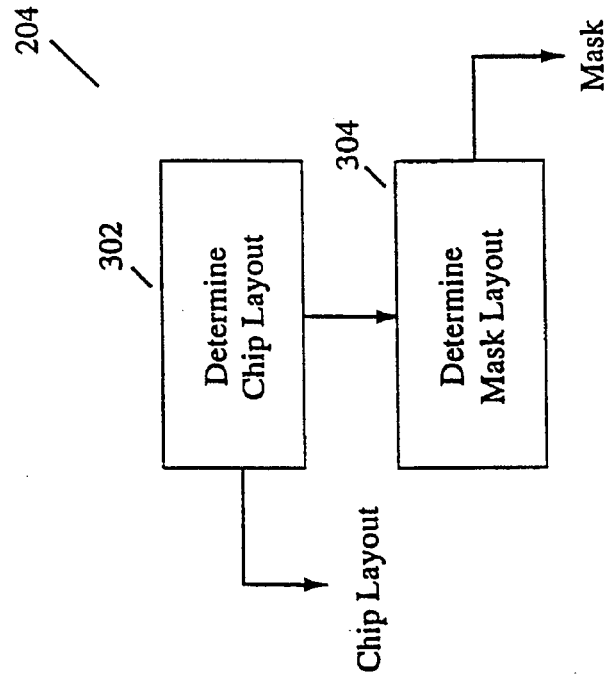
FIG. 3 illustrates the overall process of chip design.

FIG. 3 illustrates the two major layout steps performed in the design of an array of products. As shown, the system is required to determine not only the identity and layout of the probes on the chip in step 302, but also the layout of the mask at step 304. Appropriate chip and mask files are output for use in mask making, synthesis and, ultimately, data analysis.

Figure 4:
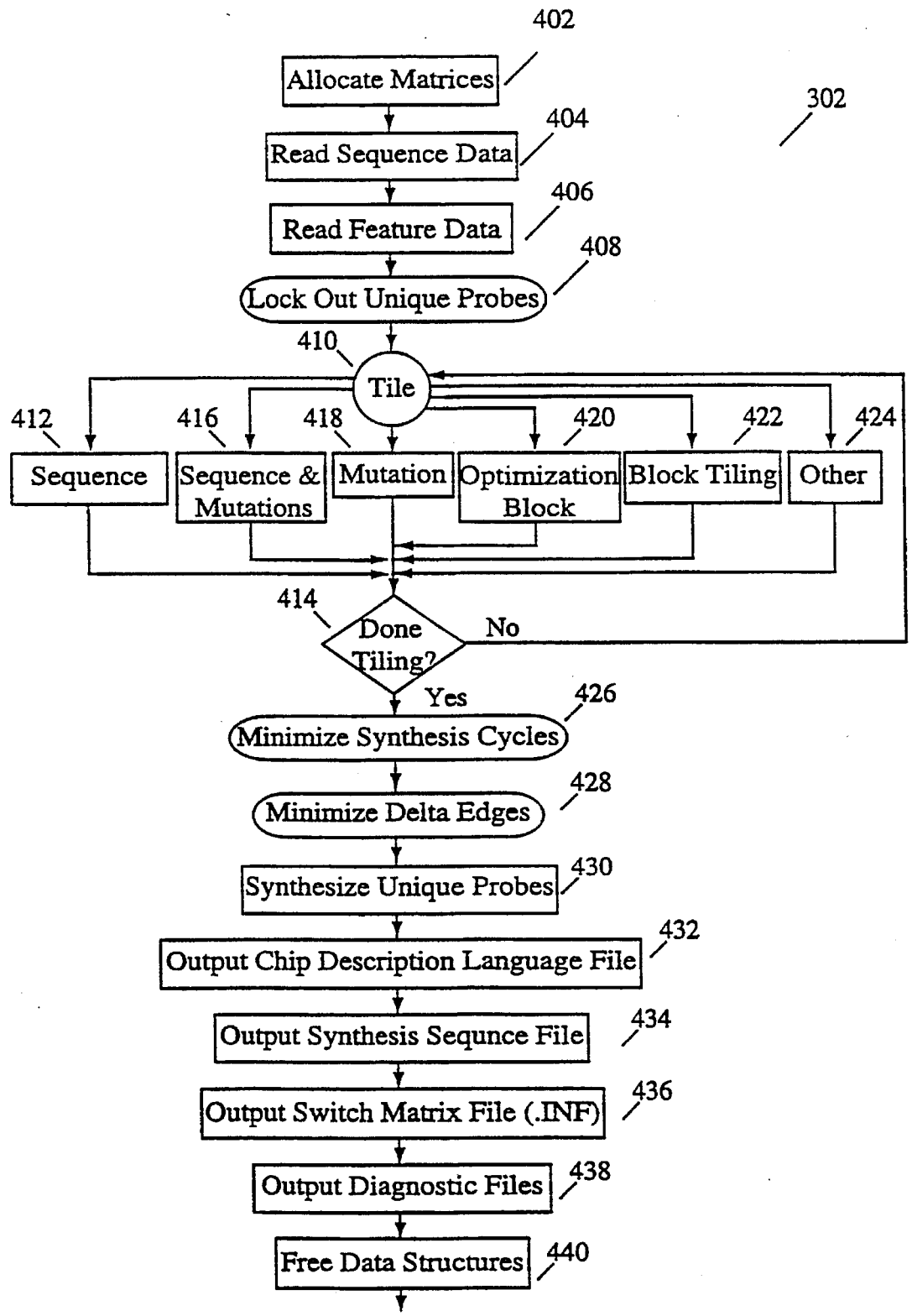
FIG. 4 illustrates the probe design and layout process in greater detail.

FIG. 4 illustrates the major operations formed in the chip layout step 302. At step 402 the system is initialized to allocate memory including a number of matrices that will be used to store various pieces of information. At step 404 the system reads the sequence data from the output of the sequence selection step 202. According to one embodiment of the invention, the sequence data will be in the form of a nucleic acid sequence, normally read into the system by way of a simple ASCii file. The text file may include other features. For example, the file may include a standardized preamble containing information such as the length of the sequence, a name or other identifier of the sequence, and other related information.

At step 406 the system reads feature data. The feature data may be, for example, the locations of introns, exons, and the lengths thereof, along with other features of a gene.

At step 408 the system locks out unique probes. During this step the system allocates spaces on the chip for probes that are not produced by tiling or other automated instructions. Examples of such probes would be user-specified primer sequences, quality control probes, or unique probes designed by the user for mutation detection. It is important to "lock out" these locations on the chip so that the automated layout of probes will not use these spaces, preventing user-specified probes from appearing on the chip at undesirable locations.

Based on the information input to the system, a tiling step 410 is then initiated. During the tiling step the sequences of various probes to be synthesized on the chip are selected and the physical arrangement of the probes on the chip is determined. For example, the target nucleic acid sequence of interest will be a k-mer, while the probes on the chip will be n-mers, where n is less than k. Accordingly, it will be necessary for the software to choose and locate the n-mers that will be synthesized on the chip such that the chip may be used to determine if a particular nucleic acid sample is the same as or different than the target nucleic acid.

In general, the tiling of a sequence will be performed by taking n-base piece of the target, and determining the complement to that n-base piece. The system will then move down the target one position, and identify the complement to the next n-bit piece. These n-base pieces will be the sequences placed on the chip when only the sequence is to be tiled, as in step 412.

As a simple example, suppose the target nucleic acid is 5'-ACGTTGCA-3'. Suppose that the chip will have 4-mers synthesized thereon. The 4-mer probes that will be complementary to the nucleic acid of interest will be 3'-TGCA (complement to the first four positions), 3'-GCAA (complement to positions 2, 3, 4 and 5), 3'-CAAC (complement to positions 3, 4, 5 and 6), 3'-AACG (complement to positions 4, 5, 6 and 7), and 3'-ACGT (complement to the last four positions). Accordingly, at step 412, assuming the user has selected sequence tiling, the system determines that the sequence of the probes to be synthesized will be 3'-TGCA, 3'-GCAA, 3'-CAAC, 3'-AACG, and 3'-ACGT. If a particular sample has the target sequence, binding will be exhibited at the sites of each 4-mer probe. If a particular sample does not have the sequence 5'-ACGTTGCA-3', little or no binding will be exhibited at the sites of one or more of the probes on the substrate.

The system then determines if additional tiling is to be done at step 414 and, if so, repeats. Additional tiling will be done when, for example, two different exons in a gene are to be tiled, or when a single sequence is to be tiled on the chip in one area, while the sequence and mutations will be tiled in another area of the chip.

If the user has determined that the sequence and its mutations are to be tiled on the chip, at step 416 the system selects probes that will be complementary to the sequence of interest, and its mutations. The sequence of the probes is determined as described above. The sequence of the mutations is determined by identifying the position or positions at which mutations are to be evaluated in the n-mer probes, and providing for the synthesis of A, C, T, and/or G bases at that position in each of the n-mer probes. Clearly, if all of the A, C, T, and G "mutations" are formed for each n-met, each tiling of wild-type and mutation probes will contain at least one duplicate region. For example, if 3'-TGCA is to be evaluated, the four "substitutions" at the second position of this probe will be 3'-TACA, TTCA, TGCA, and TCCA (with TGCA being a duplicate of the wild type). This is generally acceptable for quality control purposes and for maintaining consistency from one block of probes to the next, as will be illustrated below.

In this simple example, assuming a "4×2" tiling strategy is utilized, the system will lay out the following probes in the arrangement shown below. By a "4×2" filing strategy it means that probes of four monomers are used, and that the monomer in position 2 of the probe is varied, as shown below:

TABLE 1

5'-ACGTTGCA-3' Probe Sequences (From 3'-end)
4 × 2 Tiling

| Wild  | TGCA | GCAA | CAAC | AACG | ACGT |
|-------|------|------|------|------|------|
| A sub.| TACA | GAAA | CAAC | AACG | AAGT |
| C sub.| TCCA | GCAA | CCAC | ACCG | ACGT |
| G sub.| TGCA | GGAA | CGAC | AGCG | AGGT |
| T sub.| TTCA | GTAA | CTAC | ATCG | ATGT |

In the above "chip" the top row of probes (along with one cell below each of the four "wild" probes) should bind to a wild-type sample of DNA with the target sequence. If a sample is not of the target sequence, the top row will not generally exhibit strong binding, but often one of the probes below it will. For example, suppose a particular target sample has a mutation A in the fourth position from the 5'-end. In this case, the top row (wild) will not show strong binding in the fourth (CAAC) column on the chip, but the fourth row (T substitution) will show strong binding affinity. A "mutant" sequence in one column could, of course, also be a "wild-type" in another column. By correctly selecting the length of the probes, this problem can be reduced or eliminated.

In other embodiments the system will not tile only a few probes, but will lay out, for example, all of the possible probes of a given length. In this case, all of the evaluations will be carried out in software since the physical location of the probe on the chip may not be indicative of its relationship to the gene. For example, if all of the 4-mer probes are laid out on a chip, assume in random order, the software could simply extract the cell photon counts for the TGCA, TACA, and other probes illustrated in the above table. The data from these probes could be manipulated and even displayed as otherwise described herein, although they may not actually occupy the physical location on the chip described as preferred herein.

In many cases, it will only be desirable to provide probes for one or a few mutations. Conversely, in some cases, the user will desire the chip to have only the mutation probes on the chip. At step 418 the system will determine that the appropriate probes for synthesis be only those in selected rows/columns of the above table. For example, if the user desired to sequence probes for mutations in the second position of the target, only the sequences in the first column above would be synthesized.

At step 420 the system may lay down an optimization block. An optimization block is a specific tiling strategy designed to search a variety of probes for specific hybridization properties. One specific use of an optimization block is to find a pair of probes where one member of the pair binds strongly to the wild-type sequence, and binds minimally to a mutant sequence, while the other probe of the pair will bind strongly to the specific mutant sequence and minimally to the wild-type. The user chooses a set of lengths and locations. All possible probes for the listed lengths and positions are then formed on the chip.

At step 422 the system may do block tiling. Block tiling is a strategy in which a target is divided into "blocks" of a specified length. Each "block" of target is evaluated for variations therein. For example, suppose an 8-mer is to be evaluated. The 8-mer is to be block tiled with probes of length 5. Generally, the blocks will be overlapped such that the last base (or bases) of the first block of 5 bases is the same as the first base (or bases) of the next block. The blocks are then tiled as though they were discrete targets, with the internal bases varied through all possible mutations. For example, if 5-mer probes are used, the internal 3 bases of each block may be tiled.

A simple example is as follows. Suppose the target has the sequence 5'-ACGTTGCA-3'. The blocks would be 5'-ACGTT and 5'TTGCA. The complement to the first block would be 3'-TGCAA and the complement to the second block would be 3'-AACGT. Block 1 may be tiled for variations at the 2, 3, and 4 positions, in which case the tiling for block 1 would be as follows (with a similar tiling for block 2 normally on the same chip):

TABLE 2

Block Tiling (Block 1)

|  | Mutation at Position 2 in Block 1 | Mutation at Position 3 in Block 1 | Mutation at Position 4 in Block 1 |
|---|---|---|---|
| A sub. | 3'-TACAA | 3'-TGAAA | 3'-TGCAA |
| C sub. | 3'-TCCAA | 3'-TGCAA | 3'-TGCCA |
| G sub. | 3'-TGCAA | 3'-TGGAA | 3'-TGCGA |
| T sub. | 3'-TTCAA | 3'-TGTAA | 3'-TGCTA |

The system allows for other probe selection strategies to be added later, as indicated in step 424.

After the probes have been selected, at step 426 the system attempts to minimize the number of synthesis cycles need to form the array of probes. To perform this step, the probes that are to be synthesized are evaluated according to a specified algorithm to determine which bases are to be added in which order.

One algorithm uses a synthesis "template," preferably a template that allows for minimization of the number of synthesis cycles needed to form the array of probes. One "template" is the repeated addition of ACGTACGT. . . . All possible probes could be synthesized with a sufficiently long repetition of this template of synthesis cycles. By evaluating the probes against this (and/or other) templates, many steps may be deleted to generate various trial synthesis strategies. A trial synthesis strategy is tested by asking, for each base in the template "can the probes be synthesized without this base addition?" In other words, a "trial strategy" can be used to synthesize the probes if every base in every probe may be synthesized in the proper order using some subset of the template. If so, this base addition is deleted from the template. Other bases are then tested for removal In the specific embodiment discussed below, a synthesis strategy is developed by one or a combination of several algorithms. This methodology may be designed to result in, for example, a small number of synthesis cycles, a small number of differences between adjacent probes on the chip. In one particular embodiment, this system will reduce the number of sequence step differences between adjacent probes in "columns" of a tiled sequence, i.e., it will reduce the number of times a monomer is added in one synthesis region when it is not added in an adjacent region. These are both desirable properties of a synthesis strategy.

In order to minimize the storage requirements of the system, the various probes on the chip are internally represented by a listing of such synthesis cycles. It will be recognized that for ease of discussion, the references below still make reference to individual probes.

Once a synthesis strategy is chosen, there are still several ways to synthesize many probes. In step 428 the number of delta edges between probes is minimized. A "delta edge" is produced when a monomer is added in a synthesis region, but not in an adjacent region (a situation that is often undesirable and should be minimized if possible). It is usually desirable that the synthesis of adjacent probes vary by as few synthesis cycles as possible. Further, it is desirable that these differences be preferentially located at the ends of the probes. Accordingly, at step 428 these differences are reduced if possible.

For example, using the template ACGTACGTACG-TACGT (SEQ ID NO:1) for the synthesis of 3'-AACCTT and ACCTT, one would test the ACGT. . . template to arrive at the following base addition strategy:

| Template: | ACGTACGTACGTACGT (SEQ ID NO:1) |
| Probe 1: | A    AC    C T    T |
| Probe 2: | AC    C T    T |

Resulting in the following synthesis steps (reading from left to right in the "Probe 1" and "Probe 2" lines):

ACACTCTT

In these steps, the first A addition, the second C addition and the third T addition will be performed on both probes. However, the remaining steps will not be common to both probes, which is not desirable. Accordingly, the system would modify the strategy to be aligned as follows by "aligning" the first A addition in Probe 2 with the second addition of A in Probe 1:

| Template: | ACGTACGTACGTACGT (SEQ ID NO:1) |
| Probe 1: | A    AC    C T    T |
| Probe 2: |     AC    C T    T |

The system does this in one embodiment by scanning the chip left to right first. A block is compared to an adjacent block and the first monomer in the block is "aligned" or shifted to align with the first identical monomer in the adjacent block. All remaining monomer additions are also shifted for this block. This process is repeated left to right, right to left, and then top to bottom. Now it is seen that only the first A addition step is not common to both probes, and this step is at the end of the probes. Of course, shifting the first base addition "down" the chain one member will not always reduce the number of edges; a technique producing the minimum number of delta edges is selected.

At step 430 the software identifies the user-designated or unique probes. The unique probes are those that have been specified by the user in step 408. These probes are added after minimization of cycles and edges because the user-designated probes have been specified by the user and should not be allowed to alter the remaining portions of the chip design.

At step 432 the system outputs an appropriate description of the chip in "chip description language." Chip description language is a file format, described in greater detail below, that permits easy access to all relevant information about the sequence of a probe, its location on the chip, and its relevance to a particular study. Such information will be used in, for example, data analysis. At step 434 the system outputs a synthesis sequence file that is used by the synthesizer 112 and in later analysis steps to determine which probes were made (or are to be made) by the system. At step 436 the system outputs a switch matrix file that is also used in the mask making software 206. At step 438 output diagnostic files are provided for the user and at step 440 the system resources are released.

The synthesis sequence file contains, among other information, a listing of synthesis steps that include mask identification, monomer addition identification, exposure time, and mask location for that particular step. For example, a typical synthesis step listing in a .seq file would be:

SYNTH: A cf001a01 0 0 300

This entry indicates that reticle cf001a01 is to be used with no offset (i.e., aligned with the substrate). Entries other than 0,0 can be used to offset the x,y location of the chip, for example, for reuse of the mask in another orientation. The chip is to have a monomer "A" addition. Switch matrix files (e.g., cf274a.inf) are a set of ones and zeros, zeros indicating dark regions and ones indicating light.

Figure 5:
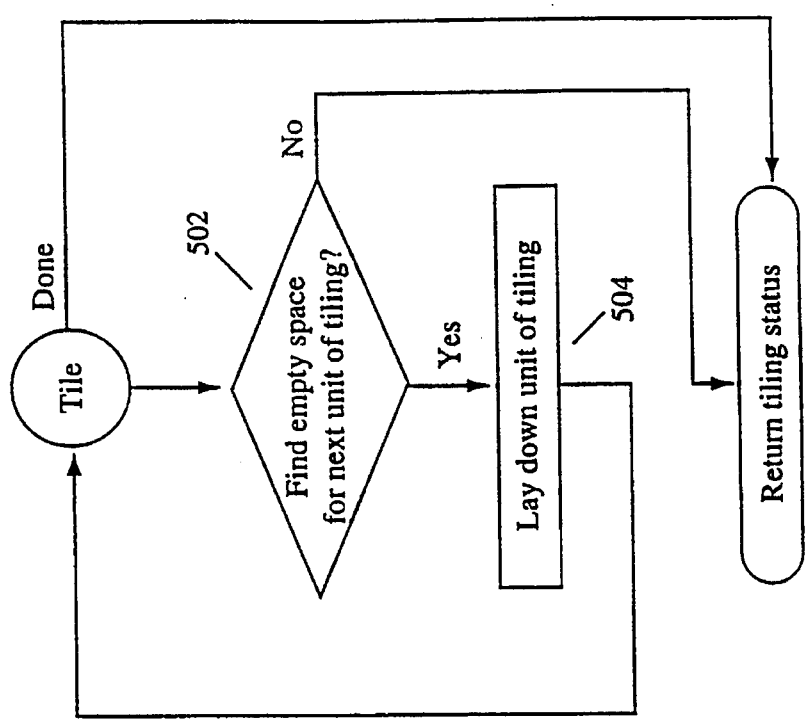
FIG. 5 illustrates the tiling strategy process in greater detail.

FIG. 5 illustrates in greater detail the process of tiling, as illustrated in step 410. The system determines which sequences are to be placed on the chip by, for example, stepping through a k-mer monomer-by-monomer, and "picking off" n-mer sections of the gene. Mutations are identified by "adding" a sequence to be tiled wherein each of A, C, T, and G (or a subset) are substituted at a predetermined location in each n-mer. The tiles are physically located by finding an unused "space" on the chip for a next unit of tiling at step 502. Then, at step 504, if there is a blank space for tiling, a particular sequence is placed in this space. If there is not another space, or when the tiling is done, the process is completed. This is performed in a series of vertical "scans" from wild-type to mutant. The particular probes placed in the tile area will represent either the sequence, the sequence and mutations, or other selected groups of probes selected by the user, as shown in FIG. 4. Reticles and chips are generally placed on the mask top to bottom, left to right.

Figure 6:
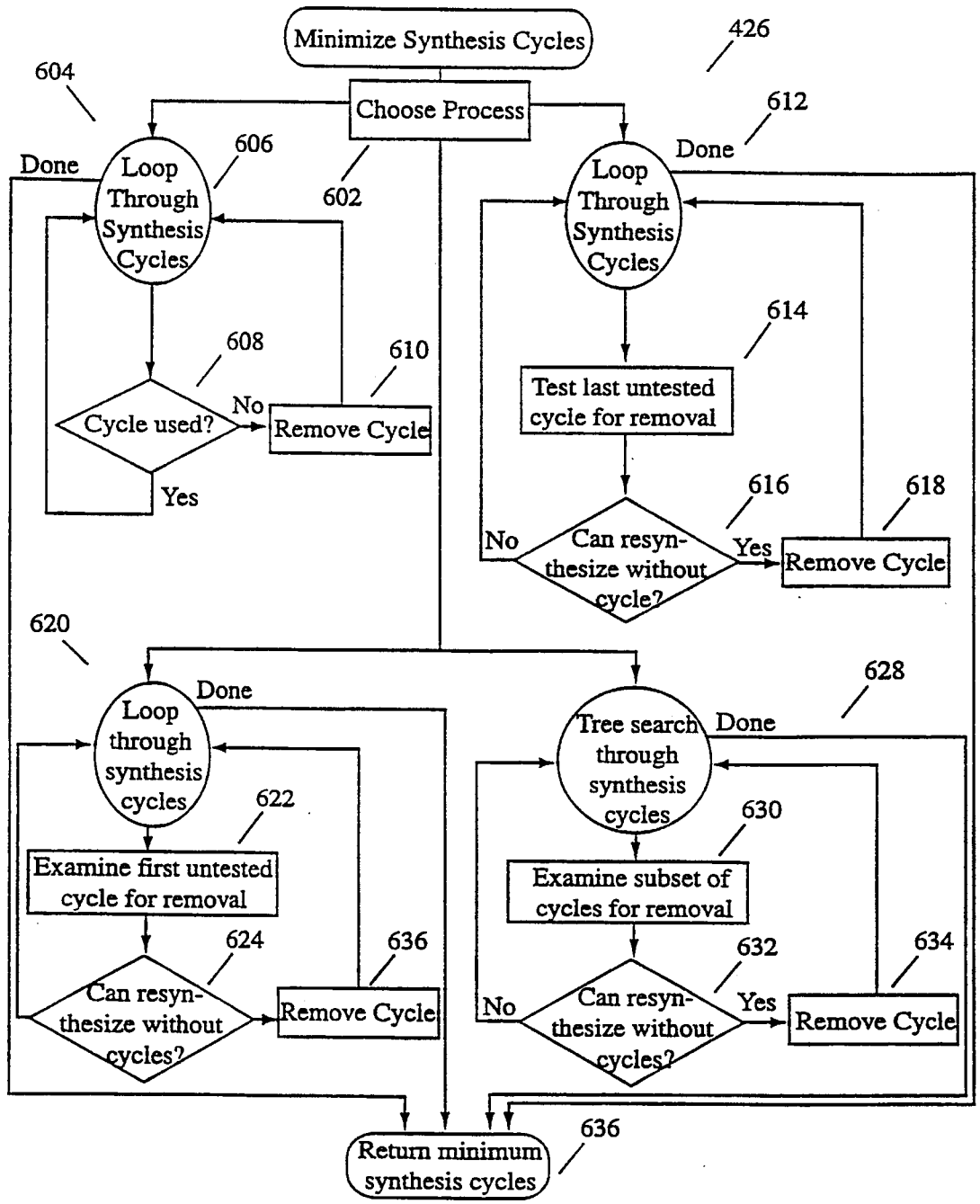
FIG. 6 illustrates techniques for minimizing the number of required synthesis cycles.

FIG. 6 illustrates the process 426 used to minimize the number of synthesis cycles. Clearly, every synthesis of, for example, DNA could be made by repeated additions of ACTGACTG... etc., for example, in which each member of the basis set of monomers is repeatedly added to the substrate. However, the synthesis of many probe arrays can be made substantially more efficient by systematically eliminating steps from this globally usable strategy. The system herein operates by using such a "template" synthesis strategy and then generates shorter trial strategies by removing cycles in some way. After cycles have been removed, the system checks to see if it is still viable for the synthesis of the particular probes in question. Various templates are tested under various algorithms until the shortest or otherwise most desirable strategy is identified.

As shown in FIG. 6, the system first determines either by default or user input which type(s) of synthesis cycle minimization process is to be utilized at step 602. The simplest process is shown by the portion of the flow chart 604 and has been briefly described above. As discussed above, at step 606, the system begins a loop in which the various probes to be synthesized on the chip are evaluated base-by-base. The system asks if a cycle is to be used at step 608. In other words, the system repetitively asks whether a particular base addition is needed in a template strategy. For example, the system may first ask if an A addition step is needed. The decision as to whether a base addition is needed is made by looking at the first base in each probe. If the base is present in any of the probes, the cycle is "needed" and this base is checked off in the probe(s) where it is being used. Also, the addition cycle is left in the synthesis. If not, the cycle is removed from the base addition sequence at step 610. The process then proceeds to compare additional base additions in the template to those monomers that have not been checked off.

The algorithm 604 results in a reasonably small number of synthesis steps, reasonable number of masks, and a relatively small number of delta edges or synthesis differences between adjacent probes on the substrate.

Algorithm 612 is particularly desirable to reduce the number of synthesis cycles. According to this algorithm, the process looks at each of the synthesis cycles in a template (such as ACGTACGT...). At step 614 the system determines, for each cycle, if it can be removed without adverse effects at step 616. If so, the cycle is removed at step 618. The decision as to whether a base addition can be removed is made by performing a sequence of steps like those in step 604 without the cycle. If the synthesis can still be performed the step is removed. Often it will be possible to remove cycles. If the base addition cannot be removed, the process repeats to the next base addition.

Optionally, algorithm 620 is also performed on the synthesis sequence. This algorithm is effectively the same as the algorithm 612, except that the process is reversed, i.e., the algorithm operates from the opposite "end" of the synthesis, reversing the order in which the various base additions are evaluated. Again, the process begins at step 622 where the next untested base addition is evaluated. At step 624 it is determined if the synthesis may be performed without the base addition cycle (by steps similar to method 604). If so, the cycle is removed at step 626. If not, the process proceeds to the next base.

Algorithm 628 is a further refinement of the process that ensures that the base addition sequence is heavily optimized. According to this algorithm, sets of multiple base additions are evaluated to see if they can be removed. For example, the algorithm may operate on two base addition steps, three base addition steps, etc. At step 630 the system evaluates the template to determine if a set of base additions can be eliminated. If the synthesis can be performed without the set of additions at step 632 they are removed at step 634. If not, the process repeats.

At step 636 the above synthesis strategies are evaluated to identify the strategy that uses the smallest number of cycles or meets other desirability criteria. That strategy is returned and used.

Figure 7:
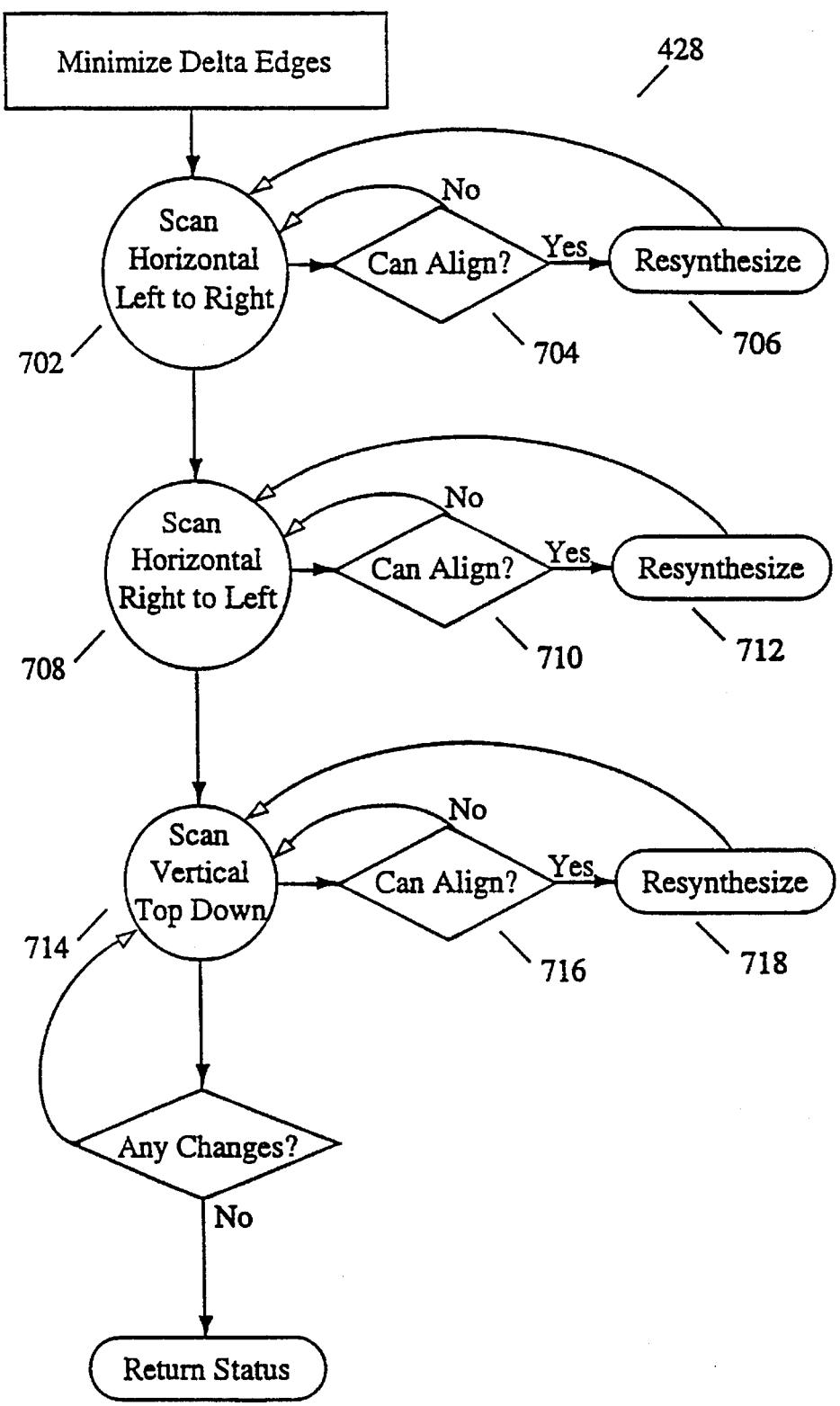
FIG. 7 illustrates a process for minimizing the changes between synthesis regions.

FIG. 7 illustrates in greater detail the process of minimizing changes (deltas) between edges. As shown in FIG. 7 the process begins by scanning the tiled chip left to right at step 702. If the next (i.e., right) "cell" can be aligned with the previous cell as per step 704 such that one or more base additions can be performed at the same time, at step 706, the cell is "resynthesized," i.e., the synthesis for that probe is altered so that the cycles it uses are aligned with the cycles used by the previous cell. A similar process is conducted at steps 708, 710, and 712 as the process evaluates cells from right to left. The process is again repeated as cells are evaluated from "top to bottom" at steps 714, 716, and 718.

This particular algorithm will function best when the chip has been tiled with probes and mutants. In other tiling strategies, the system or user will make the system use another delta edge minimization strategy. For example, when the chip is formed using block tiling, it is preferable to use an edge minimization strategy wherein all of the first bases in a block are "aligned," and all of the last bases in a block are aligned (both horizontally and vertically in a block), without shifting the entire remaining portions of the synthesis.

A simple example would be (for two of the probes tiled in Table 2, above):

| Template: | ACTGACTGACTGACTGA ... (SEQ ID NO:2) | | | |
|---|---|---|---|---|
| Probe 1: | T AC | A | A | |
| Probe 2: | TGA | A | A | |
| Probe 3: | TG C | A | A | |
| Probe 4: | T C | C | A | A |

Here, the A base at the end of probe 3 can be shifted (outward in the synthesis) to align with the A base at the end of the probe. The probes are conceptually divided for base shifting. Each base to the right of this midpoint is shifted, and each base to the left of this midpoint is not shifted. Using a midpoint to the right of the third base, the synthesis of the third probe is shifted as follows:

```
Probe 1:   T  AC  |  A A
Probe 2:   TGA    |  A A
Probe 3:   TG C   |  A A
Probe 4:   T   C  |  C A A
```

As can be seen from this step, a delta edge has been eliminated from probes 3/4. The last two "A" additions now occur at the same time. Similar shifts can be made for probes 1 and 2 as follows:

```
Probe 1:   T  AC  |  A A
Probe 2:   TGA    |  A A
Probe 3:   TG C   |  A A
Probe 4:   T   C  |  C A A
```

As seen, this process has drastically reduced the number of delta edges in even this limited probe set.

A. Chip Description Language

Chip description language (CDL) is one of the outputs of the layout program and is designed to be used by anyone who might use DNA chips. CDL is intended to be a robust description for a chip design. Each new chip design generates a file containing a description of the probes on the chip. This file may be easily used by anyone who creates DNA chips, runs experiments on chips, or analyzes the data created from the experiments. Since CDL is a generic way to describe chips, some immediate benefits include:

1) Generic Software—Software for analyzing chips need not be customized for each chip.

2) Random Placement Support—Since the probe layout information is available in the file, non-standard and even random placement of probes will not present any problems in chip analysis.

For each cell, the following fields are present in the file (an example is included in Appendix O):

X, Y—Collectively, the X and Y fields will contain a unique non-negative integer pair that describes the cells' physical locations on the chip. A record of the standard size of a block on a chip is provided in related .seq files.

Probe Sequence—The Probe Sequence field contains the design information for the probe that is laid down on the chip. This field is a sequence of bases preceded by "DL3" for example, a marker for the 3' end of the probe. In addition, the sequence will also contain a hyphen (-). The sequence to the left of the hyphen represents the smallest probe that can be synthesized at that cell location. The bases to the right of the hyphen represent the possibilities for longer probes that can be synthesized in that cell. If the probe sequence is only DL3, the cell contains a blank probe.

Design Type—The "destype" field contains an integer value indicating the strategy that created the probe. Positive integers indicate the probe is complementary to the sequence provided by the target file, and negative numbers indicate that the probe is complementary to the other strand of that sequence. The meanings of the numbers in the file are:

0=signifies no probe present in the cell;

1=signifies that this cell contains a wild-type probe from a tiling; and

2=signifies that this cell contains a mutant-type probe from a tiling.

Feature—The "feature" field contains a short string (generally one character) indicating the type of feature in the generic sequence the probe is concerned with - "I" or "E" for intron and exon, "W" or "M" for wild-type or mutant sequences.

Qualifier—This field contains a character string providing more detailed information about the feature—in the case of an intron or exon, it would contain the exon number. For probes concerned with a wild or mutant sequence, it contains a string naming the mutation.

ExPos—This field indicates a position in the sequence relative to the feature and qualifier fields. For specific mutations, this field indicates distance from the mutation position in the target sequence.

Additional fields will be added to a CDL file based on future needs. All fields must have a column header, and be separated by white space. No particular order of columns is specified—as long as every column field has the appropriate titles, compatible software will read it. No particular order of rows is specified—as long as every cell is represented, analysis may proceed. The specific layout of rows left to right, top to bottom, is designed for easy search by software.

IV. Mask Design (MaskMaker™)

Once it has been determined which probes are to be synthesized and where the various probes will be synthesized on a chip (or "substrate"), it becomes necessary to make the masks that will be used in the process of making the chips. In the manufacture of masks for use with the present invention, it is necessary for a small light beam or electron beam to scan across the surface of a chrome on glass substrate, coated with an appropriate photoresist, to define the pattern in which openings will be formed in the chrome.

It is desirable to reduce the number of "flashes" (separate exposures of the photoresist) required in making the manufacture of the mask, since the number of flashes largely determines the cost of mask manufacture. The mask makes use of a rectangular shutter that can vary in size. The light exposure can cover any rectangular block. Therefore, if the size of exposed rectangles on the mask is small, more flashes will be needed. Therefore, the cost of the mask making process is largely dependent upon the number of flashes required during mask making because the amount of time required to make the mask in modern equipment is largely proportional to the number of flashes required to make the mask.

Figure 8A:
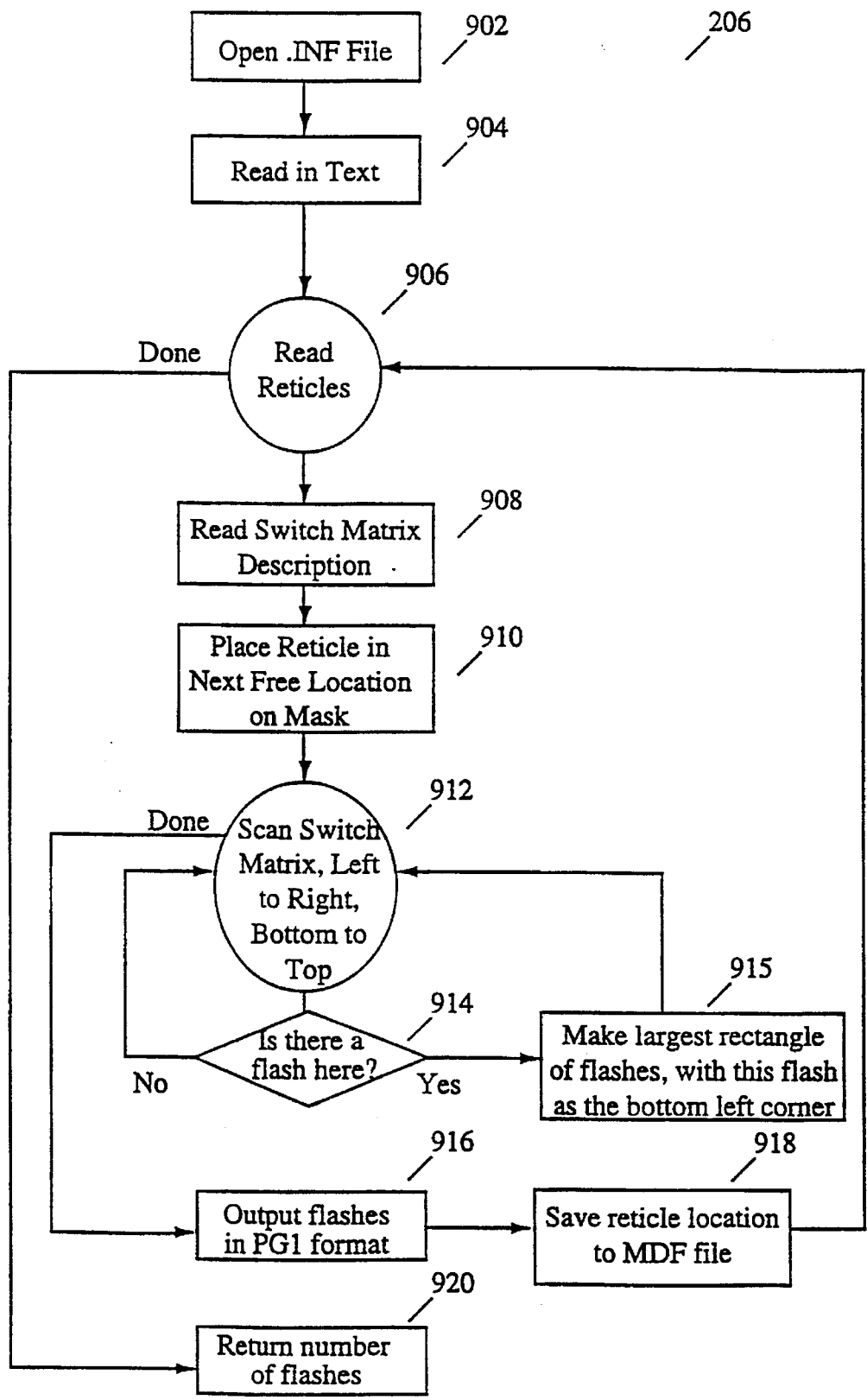
FIG. 8A illustrates a process for flash minimization.

As shown in FIG. 8A, the .inf (switch matrix) file generated at step 436 is opened at step 902. At step 904 the text from a text.inf file (the header portion of the .inf file) is read into the system. The text file will indicate where text is to be physically written onto the mask (id. numbers, etc.), as well as alignment marks. At step 906 the next reticle is read. Several reticles are read, since each mask will contain the patterns for illumination of the substrate at several steps of the fabrication, and the mask making process must be repeated for each reticle that is needed during synthesis. At step 908 the switch matrix for the next reticle is read. At step 910, the next location on the mask is identified for placement of the next reticle. At step 912 the system reads the switch matrix. The order of the switch matrix corresponds to location on the mask of light and dark regions, left to right and bottom to top. If the switch matrix indicates that the region should be opened (i.e., there should be a flash in this location), as tested by step 914, the system connects this flash with any other adjacent flashes to make the largest possible rectangle at step 915, with this flash as the bottom left hand corner. The system then repeats to step 912 until there are no additional flashes.

Figure 8B:
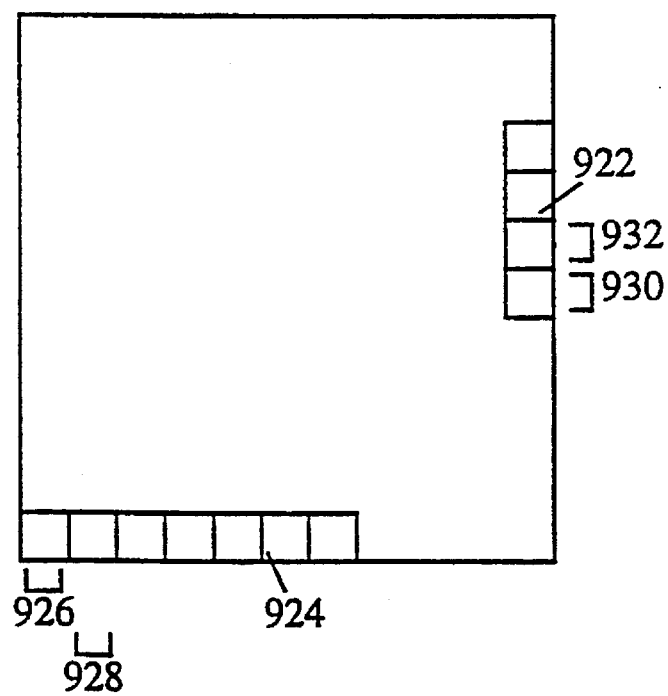
FIG. 8B illustrates a simple example of flash minimization.

FIG. 8B illustrates the process in a specific example. As shown, the system first asks if region 926 is opened. Since it is, a flash is placed here. The system then asks if region 928 is open. Since it is, a larger rectangle is formed from regions 926 and 928, and the process proceeds, creating a larger and larger rectangle until region 924 is completely formed. A rectangle is not again started until the system scans to region 930. At this time, a new rectangle is started, with this box as the bottom left hand corner. The system then scans leftwards, shifts up, and scans rightwards until reaching block 932. Again, a rectangle can be formed from regions 932 and 930, so a new rectangle is started. This process proceeds until region 922 is completely formed.

After the switch matrix has been read, the output flashes are provided in "pattern generator" (.pg1) format (a semiconductor industry standard format) at step 916. The reticle location is saved at step 918 in a .mdf file or mask definition file for use by the synthesizer. This file includes reticle names and the location of the center of the various reticles. The process is then repeated for additional reticles until the entire mask is complete. At step 920 the total number of flashes required for the mask is output for use in cost evaluation and for the information of the mask maker.

The mask definition program will provide output including the mask number and reticle locations (since multiple reticles will be included on each mask). For example, a typical mask reticle entry would include the following entry:

cf001a01:25400 37050

This information will be used by the synthesizer to locate the reticle on a particular mask. This information, along with the .seq information from the synthesis sequence file, allows the synthesis device to locate the proper mask for exposure at a particular synthesis step. Mask definition tells the synthesizer where to find the reticle. The synthesis file tells the synthesizer where a reticle is to be exposed, for how long, and with which monomer.

EXAMPLE

Figure 9A:
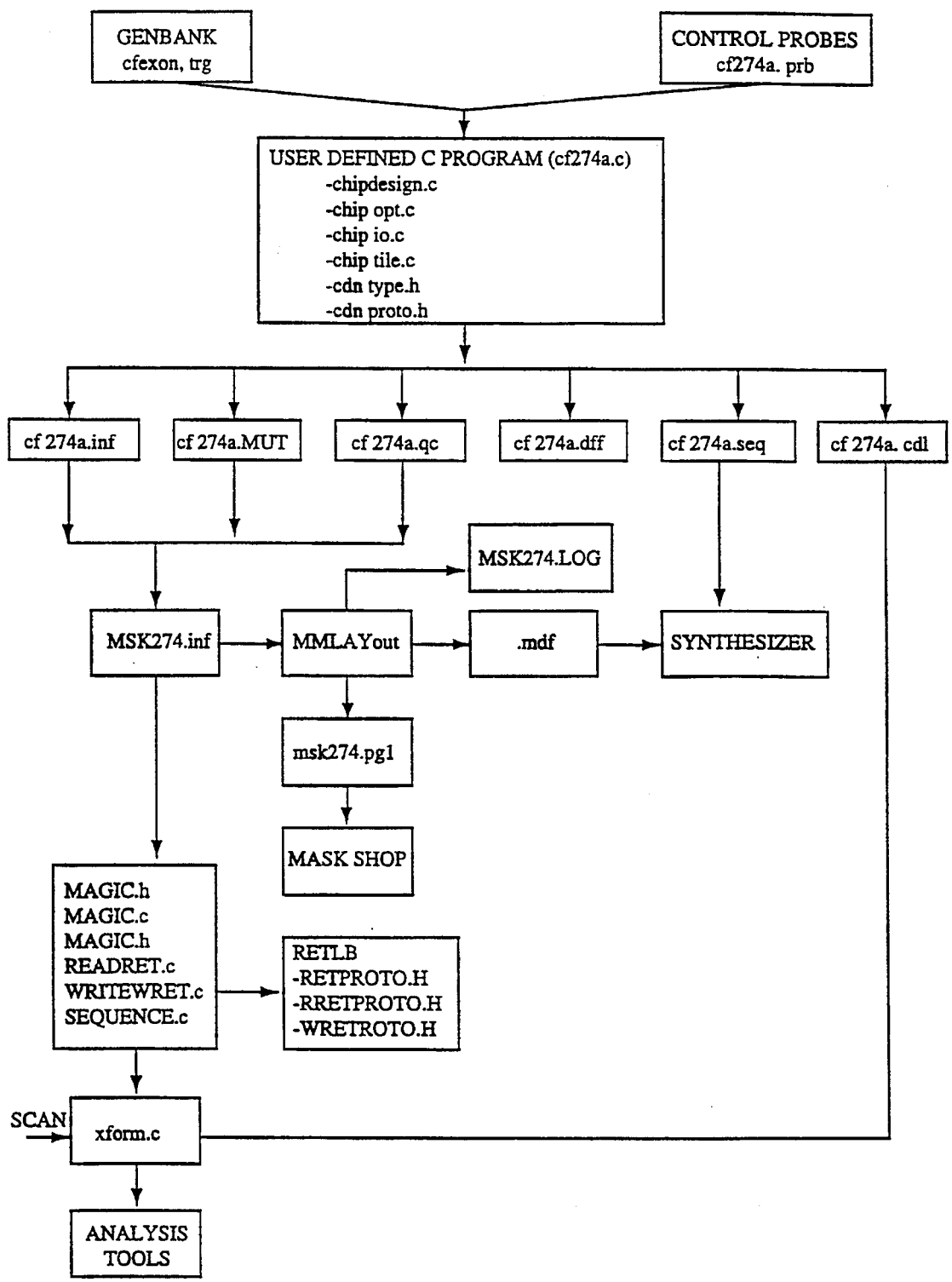
FIG. 9A illustrates organization of the appended computer files.

The Microfiche appendices to the present application provide illustrations of important input files, source files, and output files for the present inventions. FIG. 9A qualitatively illustrates the relationship of the various files. The particular example treated in this set of files would be used to generate chips useful in the diagnosis and analysis of cystic fibrosis (CF) mutations.

Appendix A is a Genbank file (cfexon.trg) identifying various CF (cystic fibrosis) mutations. Appendix B is a file (cf274a.prb) illustrating input of various control probes for CF. These are exemplary user-defined probes as used in, for example, step 430.

Appendix C is a user-defined C program (cf274a.c) that is used to direct the tiling and mask formation operations. The program calls a suite of programs including chipdesign.c (Appendix D), chipopt.c (Appendix E), chipio.c (Appendix F), chiptile.c (Appendix G), cdntype.h (Appendix H), and cdnproto.h (Appendix I) to perform the various operations discussed above. The output includes files cf274a.inf (Appendix J), cf274a.mut (Appendix K), cf274a.qc (Appendix L), cf274a.dff (Appendix M), cf274a.seq (Appendix N), and cf274a.cdl (Appendix O).

Programs cf274a.inf, cf274a.mut, and cf274a.qc are hand or automatically edited to form a file msk274.inf (Appendix P). This file is processed by programs magic.c and magic.h (Appendix Q and Appendix R, respectively) along with reticle.h, readret.c, writewret.c, and sequence.c (Appendices S, T, U, and V) to provide reticle library files (retproto.h, wretproto.h, and rretproto.h, Appendix W) and provide input, along with the .cdl file, to xform.c (Appendix X). This program appends the output of these programs with scan data in a form useful for analysis.

Figure 9B:
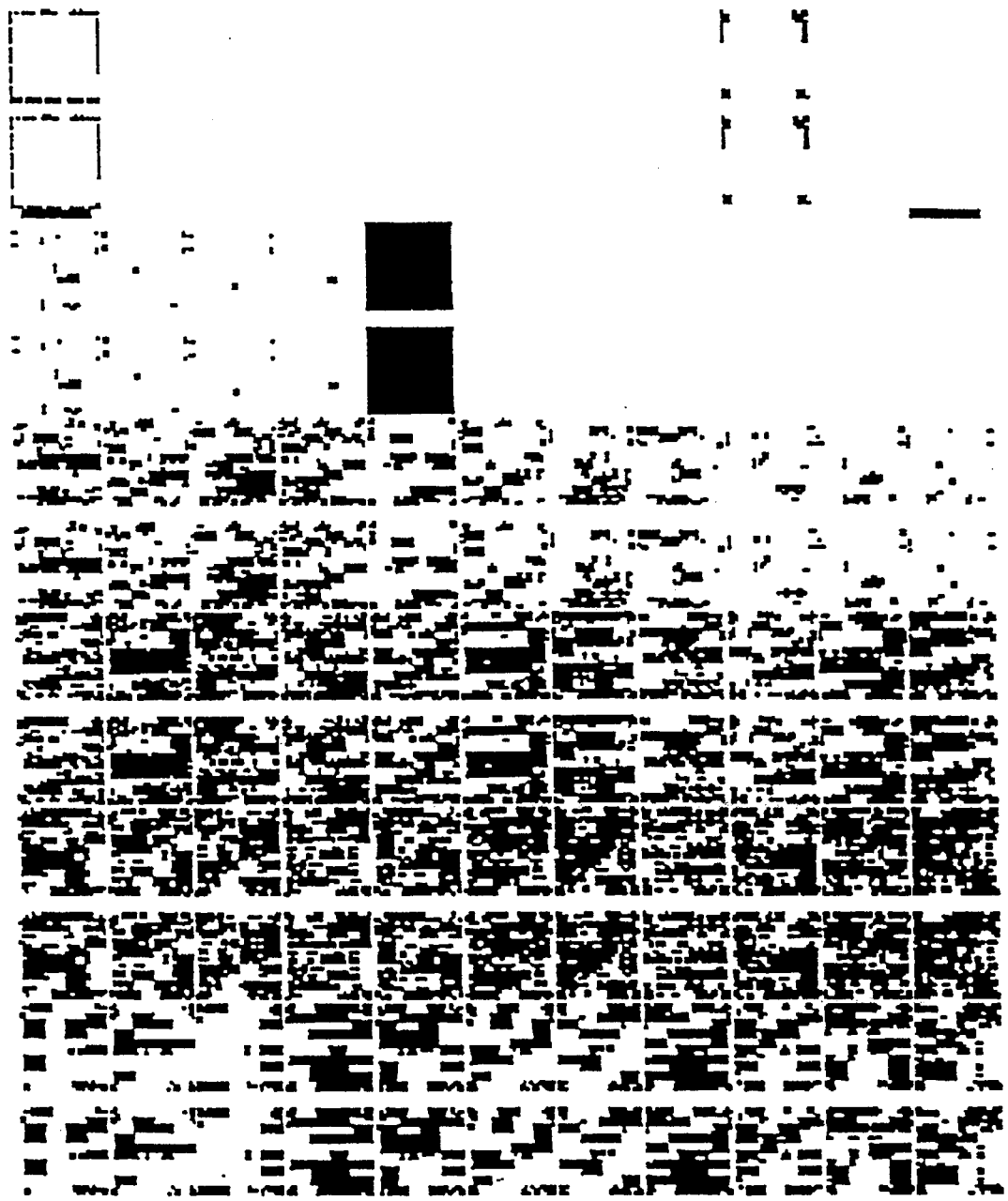
FIG. 9B illustrates typical mask output.

File msk274.inf is also used by MMLayout software (Appendix Y), including files confidnt.h, fkeys.h, make.cpp, make.h, mouse.h, text.cpp, usage.h, vga.h, and xtypes.h, to generate a mask definition file (msk274.mdf, Appendix Z) used in the synthesizer (to identify where a mask should be placed at which stage of the synthesis, etc). MMLayout also generates a file msk274.pg1 in the standard format for lithographic mask generation in a mask shop. MMLayout generates a diagnostics file msk274.log (Appendix AA) that may be used to determine if any problems arose in the mask formation process. FIG. 9B illustrates a typical mask generated as a result of the process. The various rows and columns of reticle locations on the mask can easily be identified.

V. Synthesis (Synthesizer™)

Figure 10:
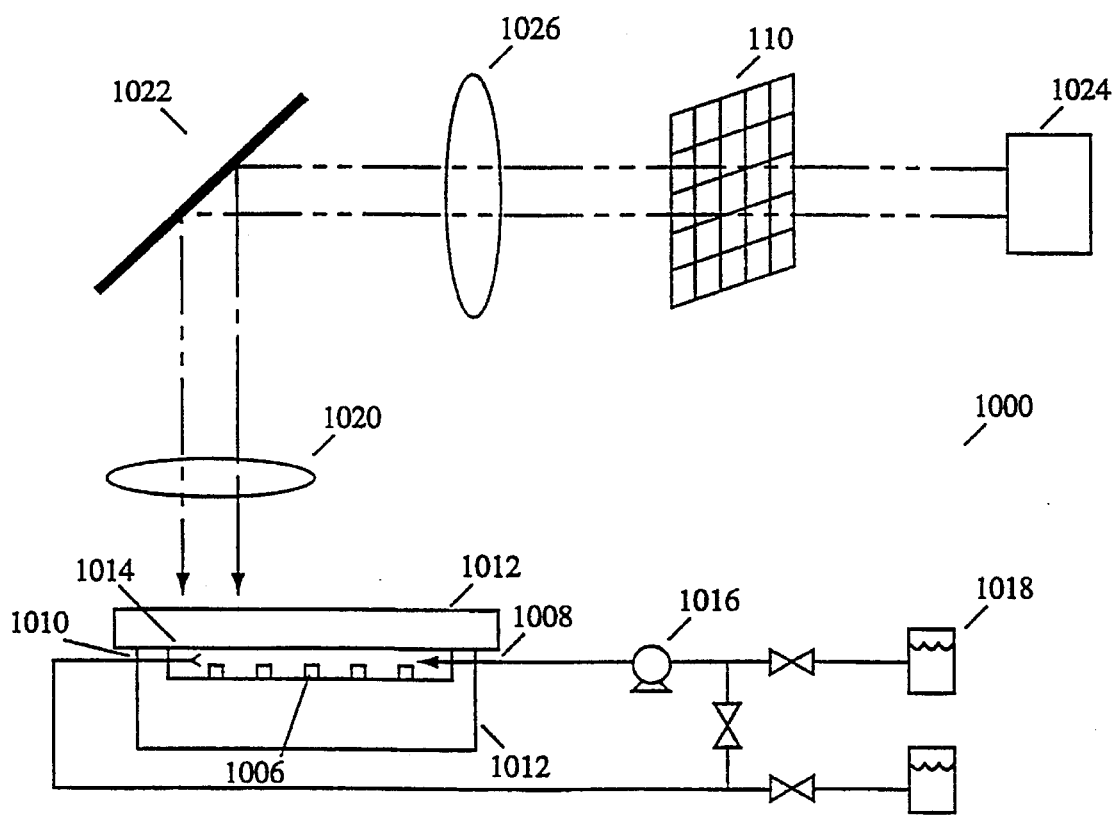
FIG. 10 illustrates a typical synthesizer.

A detailed description of the synthesis of arrays of polymeric materials is included in the disclosure of copending application Ser. No. 07/805,727, incorporated herein by reference for all purposes. FIG. 10 briefly illustrates operation of the system.

FIG. 10 schematically illustrates a preferred embodiment of a reactor system 1000 for synthesizing polymers on the prepared substrate in accordance with one aspect of the invention. The reactor system includes a body 1002 with a cavity 1004 on a surface thereof. In preferred embodiments, the cavity 1004 is between about 50 and 1000 μm deep with a depth of about 500 μm preferred.

The bottom of the cavity is preferably provided with an array of ridges 1006 which extend both into the plane of the figure and parallel to the plane of the figure. The purpose of the ridges is to generate turbulent flow for better mixing. The bottom surface of the cavity is preferably light absorbing so as to prevent reflection of impinging light.

A substrate 1012 is mounted above cavity 1004. The substrate is provided along its bottom surface 1014 with a photoremovable protective group such as MeNPOC or NVOC, with or without an intervening linker molecule. The substrate is preferably transparent to a wide spectrum of light, but in some embodiments is transparent only at a wavelength at which the protective group may be removed (such as UV in the case of MeNPOC or NVOC). The substrate in some embodiments is a conventional microscope glass slide or cover slip. The substrate is preferably as thin as possible, while still providing adequate physical support.

The substrate and the body serve to seal the cavity except for an inlet port 1008 and an outlet port 1010. The body and the substrate may be mated for sealing in some embodiments with one or more gaskets. According to a preferred embodiment, the body is provided with two concentric gaskets and the intervening space is held at vacuum to ensure mating of the substrate to the gaskets.

Fluid is pumped through the inlet port into the cavity by way of a pump 1016. Selected fluids 1018 are circulated into the cavity by the pump, through the cavity, and out the outlet for recirculation or disposal. The reactor may be subjected to ultrasonic radiation and/or heated to aid in agitation in some embodiments.

Above the substrate 1012, a lens 1020 is provided which may be, for example, a 2" 100 mm focal length fused silica lens. For the sake of a compact system, a reflective mirror 1022 may be provided for directing light from a light source 1024 onto the substrate. Light source 1024 may be, for example, a Xe(Hg) light source manufactured by Oriel and having model no. 66024. A second lens 1026 may be provided for the purpose of projecting a mask image onto the substrate in combination with lens 1020. This form of lithography is referred to herein as projection printing. As will be apparent from this disclosure, proximity printing and the like may also be used according to some embodiments.

Light from the light source is permitted to reach only selected locations on the substrate as a result of the mask 110. Light passes freely through the transparent regions of the mask, but is reflected from or absorbed by other regions. Therefore, only selected regions of the substrate are exposed to light.

In operation, the substrate is placed on the cavity and sealed thereto. All operations in the process of preparing the substrate are carried out in a room lit primarily or entirely by light of a wavelength outside of the light range at which the protective group is removed. For example, in the case of MeNPOC or NVOC, the room should be lit with a conventional dark room light which provides little or no UV light. All operations are preferably conducted at about room temperature.

A first, deprotection fluid (without a monomer) is circulated through the cavity. The slide is, thereafter, positioned in a light raypath from the mask such that first locations on the substrate are illuminated and, therefore, deprotected. The first monomer is then placed at the first locations on the substrate. After irradiation, the slide is removed, treated in bulk, and then reinstalled in the flow cell. Alternatively, a fluid containing the first monomer, preferably also protected by a protective group, is circulated through the cavity by way of pump 1016.

As the solution containing the monomer to be attached is circulated through the cavity, the nucleic acid or other monomer will react at its 3' or 5' with the 5' or 3' end of a nucleic acid on the regions of the substrate which have been deprotected. Of course, while the invention is illustrated by way of circulation of the monomer through the cavity, the invention could be practiced by way of removing the slide from the reactor and submersing it in an appropriate monomer solution.

After addition of the first monomer, the solution containing the first nucleic acid is then purged from the system. After circulation of a sufficient amount of wash solution, the mask or substrate is repositioned, or a new mask is utilized such that second regions on the substrate will be exposed to light and the light 1024 is engaged for a second exposure. This will deprotect second regions on the substrate and the process is repeated until the desired polymer sequences have been synthesized.

VI. Scanning (Photon™ and ImaGene™)

A detailed description of a device and software for scanning the synthesized chips after marking with an appropriately labelled receptor is included in copending application Ser. No. 08/195,889 (pending), filed Feb. 10, 1994, and incorporated herein by reference for all purposes.

Figure 11:
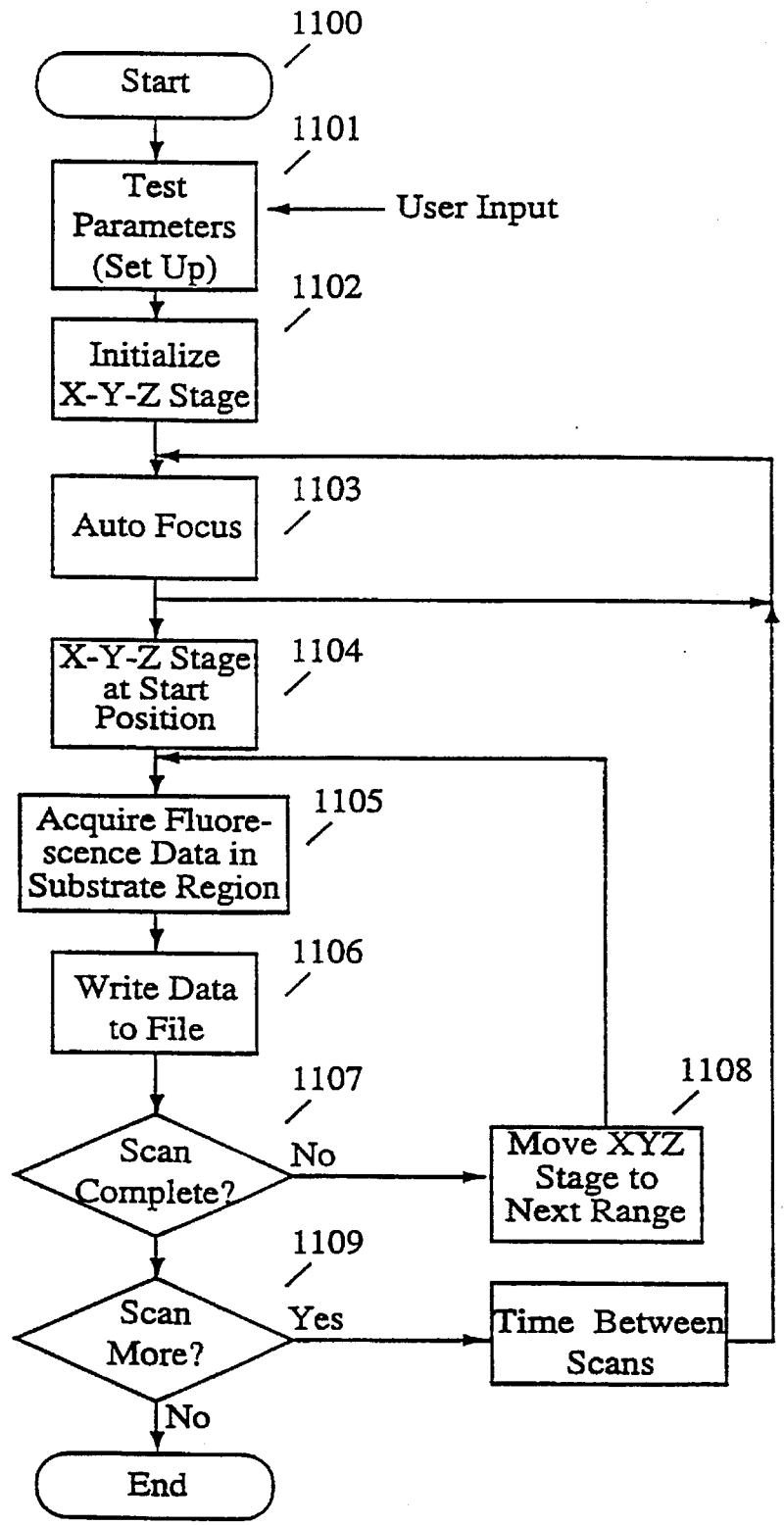
FIG. 11 illustrates operation of a typical data collection system.

FIG. 11 is a high level description of one embodiment of a scanner's operation. Referring to FIG. 11, the detection system is initialized at step 1100. At step 1101, the system prompts the user for test parameters such as:

a) temperature of the substrate;

b) pixel size;

c) scan areas;

d) scan speed;

e) number of scans to be performed; and f) time between scans.

If the user does not provide input, default values may be provided. The temperature parameter controls the temperature at which detection is performed (which may be different for each scan in a series). Preferably, detection occurs at a temperature that produces maximum binding affinity while minimizing mismatches.

Pixel size parameter dictates the size of each data collection point. It is preferable to choose a pixel size that results in at least 15 data collection points or pixels per synthesis region ("feature"). As a result, pixel size in general, is directly related to feature size. However, the number of pixels per feature size may vary according to the desires of the user.

The scan area parameter corresponds to the size of the substrate to be tested. Scan speed parameter sets the length of time the laser contacts each pixel for exciting the fluorescently-marked material. The slower the speed, the higher the excitation energy per pixel which will result in higher fluorescence count per pixel. Thus, increasing the laser power or decreasing the scan speed or a combination thereof will increase fluorescence counts per pixel. Typically, it is preferable to enter a scan speed so as to generate approximately 1000 photon counts for pixels having fluorescently-marked targets.

The number of scan parameter corresponds to the number of times the user wishes to scan the substrate. The time between scan parameter controls the amount of time to wait before commencing a subsequent scan of the substrate.

At step 1102, the system initializes the x-y-z translation table by locating the x-y-z stages at their home position. At step 1103, the system focuses the laser on the surface of the substrate. At step 1104, the system locates the x-y-z table at its start position. The system at step 1105 begins to collect data by translating the vertical stage, thereby collecting a series of data points, each data point representing the number of photon counts per pixel, which is proportional to the concentration of fluorophores for each pixel over a line. At the end of the scan line, the collected data are then written to a file, displayed, and the vertical stage retraces to its start position at step 1106. If the scan is not complete at step 1107, the x-y-z translation table moves the horizontal stage to collect data from the next line on the substrate at step 1108. Step 1105 through step 1108 are repeated for each line of data until data from all lines of the substrate have been collected. At step 1109, the system determines if more scans are to be performed according to the set up parameters. If there are, the process from step 1104 or 1103 is repeated. Otherwise, the scan is terminated.

The above description is illustrative and not restrictive. Many variations of the invention will become apparent to those of skill in the art upon review of this disclosure. Merely by way of example, while the invention is illustrated with particular reference to the evaluation of DNA, the methods can be used in the synthesis and data collection from chips with other materials synthesized thereon, such as RNA and peptides (natural and unnatural). The scope of the invention should, therefore, be determined not with reference to the above description, but instead should be determined with reference to the appended claims along with their full scope of equivalents.

What is claimed is:

1. A method of designing a synthesis method for an array of materials to be synthesized on a substrate, said array formed from groups of diverse biological materials, comprising the steps of:

inputting genetic sequences to a design computer system;

determining a sequence of monomer additions used to form said genetic sequences in said computer by the steps of:

identifying a monomer addition template; and for monomer additions in said template, determining if said monomer additions are needed in formation of said genetic sequence and, if not, removing said monomer additions from said template;

generating an output file comprising a series of desired monomer additions not removed from said template; and providing said series of monomer additions as an input file to a synthesizer.

2. The method as recited in claim 1 wherein said monomer addition template comprises repeated additions of A, C, T, and G.

3. The method as recited in claim 1 wherein said step of determining a series of monomer additions further comprises a step of optimizing said series of monomer additions, said step of optimizing further comprising the steps of:

removing a monomer addition from said template to generate a test template; and determining if said genetic sequence can be formed using said test template as said monomer addition template.

4. The method as recited in claim 3 wherein said step of removing a monomer addition is repeated for a plurality of monomer additions in said template.

5. The method as recited in claim 4 wherein said step of removing monomer additions is repeated from left to right in said template, and right to left.

6. A method of designing and using a synthesis sequence for a biological polymer comprising the steps of:

in a programmed digital computer, identifying a series of monomer additions for adjacent synthesis regions on a substrate;

adjusting said series of monomer additions to reduce the number of monomer additions that differ between at least two adjacent synthesis regions; and using said adjusted series of monomer additions to form said substrate.

7. The method as recited in claim 6 wherein differences between adjacent synthesis regions are preferentially allowed on ends of said biological polymers.

8. The method as recited in claim 6 wherein said step of adjusting said series of monomer additions comprises the steps of:

identifying at least one common monomer addition step in two adjacent synthesis regions; and shifting monomer addition steps in one of said synthesis regions such that said common monomer addition steps are performed at the same time.

9. The method as recited in claim 8 wherein said step of shifting monomer addition steps shifts all monomer addition steps in said one of said synthesis regions.

10. The method as recited in claim 8 wherein said step of shifting shifts a selected part of said monomer addition steps in said one of said synthesis regions.

11. The method as recited in claim 10 wherein said step of shifting is performed in said selected part of said monomer addition steps and a remaining part of said monomer addition steps.

12. A method of designing an array and its method of synthesis comprising the steps of:

in a computer system:
   inputting a genetic sequence file;
   identifying locations in said array for formation of genetic probes corresponding to said genetic sequence and selected mutations thereof;
   determining a sequence of monomer additions for formation of said probes and said selected mutations thereof;
   outputting at least one computer file representing said locations and said sequence of monomer additions; and
   using said at least one computer file to form said array.

13. The method as recited in claim 12 further comprising the step of minimizing differences between monomer addition steps in adjacent positions on said array.

14. The method as recited in claim 12 wherein said step of outputting at least one computer file provides a record for each synthesis region in said array comprising at least probe location, probe sequence, substitution location, and substitution base.

15. The method as recited in claim 12 wherein said step of outputting also outputs position with respect to an exon.

16. The method as recited in claim 12 wherein said step of using said at least one computer file further comprises the steps of using said computer file to design a series of reticles for synthesizing said array;

using said series of reticles to selectively expose a surface of a substrate to light, exposing reactive groups; and exposing said surface to selected monomers.

* * * * *

UNITED STATES PATENT AND TRADEMARK OFFICE
CERTIFICATE OF CORRECTION

PATENT NO. : 5,593,839
APPLICATION NO. : 08/460411
DATED : January 14, 1997
INVENTOR(S) : Hubbell et al.

It is certified that error appears in the above-identified patent and that said Letters Patent is hereby corrected as shown below:

Column 1, Lines 6-10 of the Specification, the Government Rights Notice, please replace the paragraph:
"Portions of the material in this specification arose in the course of or under contract nos. 92ER81275 (SBIR) between Affymetrix, Inc. and the Department of Energy and/or H600813-1, -2 between Affymetrix, Inc. and the National Institutes of Health."
with the paragraph:
-- Portions of the material in this specification arose in the course of or under contract nos. 92ER81275 (SBIR) between Affymetrix, Inc. and the Department of Energy and/or HG00813-1, -2 between Affymetrix, Inc. and the National Institutes of Health. The Government has certain rights in this invention. --

Signed and Sealed this

Seventeenth Day of October, 2006

JON W. DUDAS
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:1:

ACGTACGTAC GTACGT                                                                          1 6

( 2 ) INFORMATION FOR SEQ ID NO:2:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (oligonucleotide)

( x i ) SEQUENCE DESCRIPTION: SEQ ID NO:2:

ACTGACTGAC TGACTGA                                                                       1 7